US011402390B2

(12) United States Patent
Stolz et al.

(10) Patent No.: US 11,402,390 B2
(45) Date of Patent: Aug. 2, 2022

(54) METHOD FOR ASSAYING LOWER RESPIRATORY TRACT INFECTION OR INFLAMMATION

(71) Applicants: STEPSTONE DIAGNOSTICS SARL, Geneva (CH); LASCCO SA, Epalinges (CH)

(72) Inventors: Daiana Stolz, Arlesheim (CH); Frederic Lajaunias, Geneva (CH)

(73) Assignees: UNIVERSITY HOSPITAL OF BASEL, Basel (CH); Lascco SA, Epalinges (CH)

( * ) Notice: Subject to any disclaimer, the term of this patent is extended or adjusted under 35 U.S.C. 154(b) by 380 days.

(21) Appl. No.: 15/911,347

(22) Filed: Mar. 5, 2018

(65) Prior Publication Data

US 2018/0259532 A1    Sep. 13, 2018

Related U.S. Application Data

(63) Continuation of application No. 13/701,433, filed as application No. PCT/IB2011/052381 on May 31, 2011, now abandoned.

(60) Provisional application No. 61/349,909, filed on May 31, 2010.

(51) Int. Cl.
*G01N 33/58* (2006.01)
*G01N 33/68* (2006.01)

(52) U.S. Cl.
CPC ........ *G01N 33/6893* (2013.01); *G01N 33/581* (2013.01); *G01N 2333/47* (2013.01); *G01N 2800/12* (2013.01); *G01N 2800/122* (2013.01)

(58) Field of Classification Search
CPC ......... G01N 2800/12; G01N 2800/122; G01N 2333/47; G01N 33/581; G01N 33/6893
See application file for complete search history.

(56) References Cited

U.S. PATENT DOCUMENTS

| 5,789,261 | A  | * | 8/1998  | Schwartz ......... G01N 33/54393 436/518 |
| 6,309,888 | B1 | * | 10/2001 | Holvoet ............. G01N 33/6893 435/7.1 |
| 7,358,062 | B2 | * | 4/2008  | Suovaniemi ..... G01N 33/56922 424/234.1 |
| 2007/0224638 | A1 | | 9/2007 | Melanitou-McClymont |
| 2010/0222223 | A1 | | 9/2010 | Graf et al. |
| 2013/0165345 | A1 | | 6/2013 | Halangk |

FOREIGN PATENT DOCUMENTS

| WO | 2008021290 A2 | 2/2008 |
| WO | 2008085601 A2 | 7/2008 |
| WO | 2009030456 A1 | 3/2009 |

OTHER PUBLICATIONS

Harlow, E. and Lane, D., Antibodies: A Laboratory Manual (1988) Cold Spring Harbor Laboratory Press, Cold Spring Harbor, NY, pp. 553, 556, and 578-581.*
Database Geneseq [Online], Sep. 18, 2008 (Sep. 18, 2008), "Human asthma disease treatment associated protein, SEQ ID 698.", XP000002657057, retrieved from EBI accession No. GSP: ASQ27792, Database accession No. ASQ27792 sequence.
Database Geneseq [Online], Feb. 3, 2011 (Feb. 3, 2011), "Human pancreas-specific protein, SEQ: 18900.", XP000002657056, retrieved from EBI accession No. GSP: AUN17559, Database accession No. AUN17559 sequence.
Carrere J et al: "Immunoreactive pancreatic Reg protein in sera from cystic fibrosis patients with and without pancreatic insufficiency", GUT, vol. 44, No. 4, Apr. 1999 (Apr. 1999), ISSN: 0017-5749 abstract.
Blasi F et al: "Biomarkers in lower respiratory tract infections", Pulmornary Pharmacology & Therapeutics, Academic Press, GB, vol. 23, No. 6, Dec. 1, 2010 (Dec. 1, 2010), pp. 501-507.
De Reggi M et al: "Protein-X, pancreatic stone-, pancreatic thread-, reg-protein, P19, lithostathine, and now what? Characterization, structural analysis and putative function(s) of the major non-enzymatic protein of pancreatic secretions", Current Protein and Peptide Science, vol. 2, No. 1, Mar. 2001 (Mar. 2001) pp. 19-42.
Combes Alain et al: "Early predictors for infection recurrence and death in patients with ventilator-associated pneumonia.", Critical Care Medicine Jan. 2007 LNKD-PUBMED: 17080004, vol. 35, No. 1, Jan. 2007 (Jan. 2007) pp. 146-154.
Zhang Yu-Wei et al: "Reg gene family and human diseases", World Journal of Gastroentronology : WJG Dec. 2003 LNKD-PUBMED: 14669303, vol. 9, No. 12, Dec. 2003 (Dec. 2003), pp. 2635-2641.
Boeck et al. "Pancreatic Stone Protein: a marker of organ failure and outcome in ventilator-associated pneumonia" Chest. Oct. 2011; 140(4):925-32. dol: 10.1378/chest .11-0018. Epub Aug. 11, 2011.
Nakae et al. "Molecular Forms of Serum Pancreatic Stone Protein in Acute Pancreatitis" International Journal of Pancreatology, vol. 25, No. 1, 17-21, Feb. 1999.
Satomura et al. "Measurement of serum PSP/reg-protein concentration in various diseases with a newly developed enzyme linked immunsorbent assay" J. Gastroenterol 1995; 30:643-650).
Planas et al, "Regenerating gene la is a biomarker for diagnosis and monitoring of celiac disease; a preliminary study" Transl Res. Sep. 2011; 158(3): 140-5, dol :10.1016/j.trsl.2011.04.004. Epub May 30, 2011, doi:10. 1016/j.trsl.2011.04.004.
Micek et al. Health Care-Associated Pneumonia and Community-Acquired Pneumonia a Single-Center Experience Antimicrobial Agents and Chemotherapy, Oct. 2007, p. 3568-3573.

(Continued)

*Primary Examiner* — Galina M. Yakovleva
(74) *Attorney, Agent, or Firm* — Agris & von Natzmer LLP; Joyce von Natzmer

(57) ABSTRACT

The present invention relates to a reliable method of prediction of lower respiratory tract infection or inflammation in humans, wherein the level of pancreatic stone protein/regenerating protein (PSP/reg) is determined in serum, and a high level is indicative of the development and the severity of the disease, allowing the classification of patients according to risk.

12 Claims, 4 Drawing Sheets

Specification includes a Sequence Listing.

(56) References Cited

OTHER PUBLICATIONS

Mayeux et al. "Biomarkers: Potential uses and Limitations"; NeuroRx (2004); vol. 1, pp. 182-188.
LaBaer et al. Journal of Proteoma Research 2005, 4 1053-1059.
Fujishiro et al. "Regenerating gene (REG) 1 alpha promotes pannus progression in patients with rheumatoid arthritis" Mod Rheumatol Apr. 2012,22(2):228-37. dol: 10.1007/s10165-011-0564-y. Epub Dec. 28, 2011.
Satomura et al. "Measurement of serum PSP/reg-protein, concentration in various diseases with a newly developed enzyme-linked immunocorbent assay" J Gastroenterol 1995: 30:643-650.
Bonten et al. "The Systemic Inflammatory Response in the Development of Ventilator-Associated Pneumonia" Am J Respir Crit Care Med vol. 156. pp. 1105-1113, 1997.
Seligman et al. "Copeptin, a noval prognostic biomarker in ventilator-associated pneumonia" Critical Care 2008, 12-R11 (dol:10.1186/cc6780), 9 pages.
Bimmler et al. "Regulation of PSP/reg in rat pancreas: immediate and steady-state adaptation to different diets", Pancreas Oct. 1999; 19(3):255-67.
Graf et al. "Coordinate Regulation of Secretory Stress Proteins (PSP/reg. PAP I, PAP II, and PAP III) in the Rat Exocrine Pancreas during Experimental Acute Pancreatitis" Journal of Surgical Research 105,136-144 (2002).

\* cited by examiner

METHOD FOR ASSAYING LOWER RESPIRATORY TRACT INFECTION OR INFLAMMATION

FIELD OF THE INVENTION

The present invention relates to a method of prognosis or survival prediction and/or diagnosis of infections or inflammatory diseases of the airways and lungs, in particular for prognosis of the development of acute exacerbation of chronic obstructive pulmonary disease (AECOPD) or ventilator associated pneumonia (VAP). The invention allows for the determination of the level of pancreatic stone protein/regenerating protein (PSP/reg) in body fluid samples of a patient and sorting patients according to risk.

BACKGROUND OF THE INVENTION

Lower respiratory tract infections, i.e. acute bronchitis, acute exacerbations of chronic obstructive pulmonary disease (COPD) or pneumonia, account for almost 10% of the worldwide burden of morbidity and mortality. Detecting the presence, defining the cause, and predicting the severity of lower respiratory tract infections are constant challenges for the treating clinician. Among the most commonly used biomarkers for the detection and management of lower respiratory tract infections are leukocyte counts, C-reactive protein, and procalcitonin. Unfortunately, none of these biomarkers is completely satisfying.

Pancreatic stone protein/regenerating protein (PSP/reg) belongs to a family of lectin-binding proteins that were identified initially in patients with pancreatitis (L. Multigner et al., *Gastroenterology* 1985; 89:387-391). PSP/reg has been studied predominantly in the pancreas. Under conditions of acute or chronic pancreatitis, it is highly up-regulated and may appear in the serum (W. Schmiegel et al., *Gastroenterology* 1990; 99:1421-1430). Serum levels are also raised in several gastrointestinal diseases (Satomura et al., *J Gastroenterol* 1995, 30:643-650). The function of PSP/reg is still highly debated, but it is generally assumed that it is involved in promoting cell proliferation during regenerative processes (Y. Kinoshita et al., *J. Gastroenterol* 2004, 39:507-513). Although this protein is a secretion product, its expression is not induced by diet alone. In trauma patients, it has been shown that PSP/reg is up-regulated in blood after trauma, and that the PSP/reg level is related to the severity of inflammation. In particular, it is highly increased in patients during sepsis (M. Keel et al., *Crit Care Med.* 2009 37(5):1642-8).

SUMMARY OF THE INVENTION

The present invention relates to a method of prediction and/or diagnosis of infections or inflammatory diseases of the airways and lungs in human, in particular for the prediction of the development and the severity and prognosis of low respiratory tract infection or inflammatory disease including COPD or VAP, wherein the level of PSP/reg is determined in a body fluid sample, and a high level is indicative of the development and the severity of lower respiratory tract infections at early stages of the disease. In addition, in the present invention, high levels of PSP/reg are predictive of survival in ventilator-acquired pneumonia and correlate with clinical score. Also, high levels of PSP/reg allow detecting COPD patients with positive sputum microbiology.

DESCRIPTION OF THE FIGURES

FIG. 3A). 177 ng/ml at day 7 was the best threshold to predict death with a sensitivity of 54% and a specificity of 90% (AUC: 0.76; FIG. 3B).

DETAILED DESCRIPTION OF THE INVENTION

Figure 1:
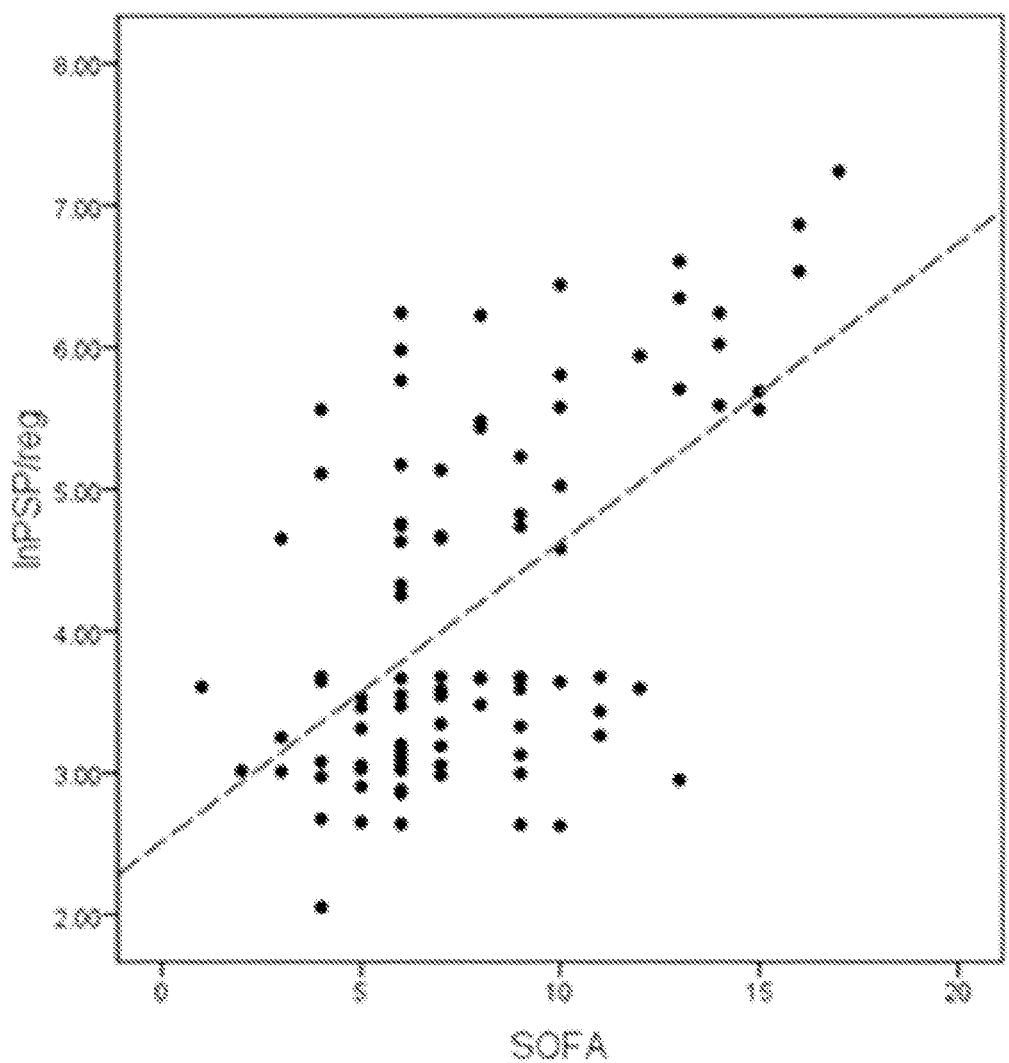
FIG. 1: Correlation of SOFA and ln(PSP/reg serum levels) at VAP-onset ($p<0.001$) in 101 VAP patients. PSP/reg was logarithmized for graphical demonstration. Regression line (dashed line).

The present invention relates to a method of prognosis and/or diagnosis of infections or inflammatory diseases of the airways and lungs in humans wherein the level of pancreatic stone protein/regenerating protein (PSP/reg) is determined in a body fluid sample, and a high level is indicative of the development and the severity of the disease. In a first aspect, the invention relates to an ex-vivo method for detecting and/or diagnosing infections or inflammatory diseases of the airways and lungs in humans. In particular, the present method according to the invention allows the prediction of the severity and the prognosis of infections and/or inflammatory diseases of the low respiratory tract including COPD and VAP. The methods according to the present invention comprise determining the level of PSP/reg in an isolated body fluid sample, e.g. serum, wherein said level is indicative of the severity of lower respiratory tract infections and/or inflammations at early stages of the disease and of the complications and risk of mortality linked to said infections and/or inflammations.

As defined herewith, "patient" refers to any mammalian animal including human, dog, cat, cattle, goat, pig, swine, sheep and monkey. Patients are preferably humans.

As defined herewith, "lower respiratory tract infection" refers to an infection in the airways or lungs caused by bacteria, viruses, fungi or parasites. It includes, for example, acute and chronic bronchitis, community-acquired pneumonia, which can be caused, among others, by *Streptococcus pneumoniae*, atypical bacteria, gram-negative bacteria, or *Haemophilus influenza*, hospital-acquired pneumonia such as ventilator associated pneumonia (VAP), chronic obstructive pulmonary disease (COPD), acute exacerbation chronic obstructive pulmonary disease (AECOPD), bronchiectasis including cystic fibrosis and interstitial lung disease.

As defined herewith, "ventilator associated pneumonia (VAP)" is a pneumonia that develops 48 hours or longer after mechanical ventilation and that is characterized by an invasion of the lower respiratory tract and lung parenchyma by microorganisms. VAP is a potentially serious medical condition than can lead to sepsis through the development of a systemic infection that affects a number of organs and tissues, or affects the body as a whole.

As defined herewith, "chronic obstructive pulmonary disease (COPD)" is characterized by a severe obstruction of the airflows that cause an abnormal inflammatory response in the lung. Generally, patients suffer exacerbations that can be triggered by infection or air pollution, and that lead to AECOPD (acute exacerbation COPD) a critical condition requiring hospitalization. COPD can be classified into 4 stages correlated with severity (minor, moderated, severe, and very severe) (Gomez and Rodriguez-Roisin, Curr. Opin. Pulm. Med. 2002: 8(2): 81-86).

As defined herewith, "acute exacerbation COPD (AECOPD)" is a sudden worsening of COPD symptoms, like shortness of breath, quantity and color of phlegm, that typically lasts for several days. It may be triggered by an infection with bacteria or viruses or by environmental pollutants.

In VAP, the infection occurs consequently to surgery, in particular consequently to an intubation for mechanical ventilation given by means of an endotracheal tube or tracheotomy. In COPD, the infection can also occur consequently to an obstruction of the airways in the lung. The infection can originate from the respiratory tract.

As defined herewith, PSP/reg refers to human pancreatic stone protein, also called regenerating gene (REG) I protein or lithostatine or pancreatic thread protein (Gross al., *J. Clin. Invest.*, 1985: 76, 2115-2126) and can be the isoform alpha (Uniprot sequence number: P05451 also identified herewith as SEQ ID NO. 1) or beta (Uniprot sequence number: P48304 also identified herewith as SEQ ID NO. 2).

As defined herewith body sample refers to any sample that is obtained from the patient's body. Body sample includes body fluid samples and extracts from solid tissue or from fecal matter. Body fluid samples include, for instance, samples of whole blood, serum, plasma, urine, sputum, cerebrospinal fluid, tear fluid, sweat, or milk.

One aspect of the invention relates to a method of prognosis and/or diagnosis of infections or inflammatory diseases of the airways and lungs in a patient, preferably a human, wherein the level of pancreatic stone protein/regenerating protein (PSP/reg) is determined in a body fluid sample or in a solid body tissue, and a high level is indicative of the development and the severity of the disease.

In a further aspect of the method of the invention, the infection in the airways or lungs is caused by bacteria, viruses, fungi, or parasites, and is selected from the group of low respiratory tract infections, particularly acute and chronic bronchitis, acute exacerbation of COPD, stable COPD, community or hospital-acquired or ventilator associated pneumonia, sarcoidosis, bronchiectasis, including cystic fibrosis and interstitial lung disease and asthma.

In another aspect, the present invention is directed to an ex-vivo method of prognosis and/or diagnosis of infections or inflammatory diseases of the airways and lungs in a patient, or an ex-vivo method for detecting the development of infections or inflammatory diseases of the airways and lungs in a patient, comprising determining the level of pancreatic stone protein/regenerating protein (PSP/reg) in a body fluid sample from said patient. The patient is preferably a human.

In another aspect of the method of the invention, the PSP/reg protein has the amino acid sequence of SEQ ID NO:1 or SEQ ID NO: 2.

In a preferred aspect, the method of the invention is for the diagnosis and prognosis of lower respiratory tract infection, preferably pneumonia, preferably VAP or COPD and AECOPD.

According to a further aspect, the method of the invention is an in vitro diagnostic method.

In a still further aspect, the present invention relates to an ex-vivo method of prognosis and/or diagnosis of infections or inflammatory diseases of the airways and lungs in a patient, or to an ex-vivo method for detecting the development of infections or inflammatory diseases of the airways and lungs in a patient, comprising:

a) providing a body fluid sample from said patient;
b) determining the level of PSP/reg in said sample;
c) comparing the level of PSP/reg determined in step b) with a reference value;

wherein a higher level of PSP/reg determined in step b), compared to the reference value, is indicative of the severity of the infection and/or inflammatory disease and predictive of the outcome.

According to another aspect of the invention, the method of the invention is an in vitro diagnostic method.

In a specific aspect of the invention, the reference value is the level of PSP/reg measured in a body fluid sample from a patient without known or suspected infection.

In another aspect of the invention, the reference value is about 10 ng/ml.

In a further aspect of the invention, the reference value is 25 ng/ml. In a still further aspect of the invention, the reference value is 180 ng/ml, more preferably 200 ng/ml.

In another specific aspect of the invention, the body fluid sample is serum or plasma. Other body fluids than serum and plasma useful for determination of PSP/reg levels are e.g. whole blood, urine, sputum, cerebrospinal fluid, tear fluid, sweat, milk, or extracts from solid tissue or from fecal matter.

In COPD patients, the PSP/reg level indicative for bacterial exacerbation in blood serum and plasma is of, or about, 25 ng/ml or more than 25 ng/ml at exacerbation. Hence, more specifically, the invention relates to a method for detecting the presence of positive bacterial sputum as a cause of the exacerbation, wherein the level of PSP/reg is determined preferably in serum or plasma, and a level of, or about, 25 ng/ml or more, is indicative of positive sputum microbiology. Preferably, a PSP/reg level in serum or plasma that is equal to, or higher than, about 30 ng/ml is indicative of bacterial exacerbation in COPD patients.

Also, preferably, the PSP/reg level is determined at exacerbation of COPD, or on the day of admission to the hospital following exacerbation.

In VAP patients, the PSP/reg level indicative for severe complications and patient outcome, in blood serum and plasma, is of or about 180 ng/ml or more than 180 ng/ml at VAP onset, or at day 2, 3, 4, 5, 6, 7, after a VAP onset that occurred at day 0. Hence, more specifically, the invention relates to a method to identify individuals with a particular good and poor outcome and hence to predict severity of infection, wherein the level of PSP/reg is determined in serum or plasma. A PSP/reg level in serum or plasma of, or below, 24 ng/ml is associated with a good chance of survival, whereas a PSP/reg level of, or higher than, 180 ng/ml is indicative of a very poor outcome and high risk of mortality. Preferably, a PSP/reg level of about, or higher than, 200 ng/ml or more preferably higher than 250 ng/ml is indicative of severe complications and poor outcome. Preferably, the PSP/reg level is determined at exacerbation or at day 2, 3, 4, 5, 6, 7 after VAP onset.

In a preferred aspect of the ex-vivo method of the invention, the level of PSP/reg determined in step b) is determined on the day of VAP onset or on day 2, 3, 4, 5, 6, 7 after onset as compared to a reference value of, or about, 10 ng/ml.

In an alternative preferred aspect of the ex-vivo method of the invention, the level of PSP/reg determined in step b) is determined on the day of, or on the day of admission to the hospital for, exacerbation of COPD as compared to a reference value of, or about, 10 ng/ml.

Any known method may be used for the determination of the level of PSP/reg in body fluids. Methods considered are e.g. Enzyme-linked immunosorbent assay (ELISA), Radioimmunoassay (RIA), Enzymoimmunoassay (EIA), mass spectrometry, or microarray analysis. Such methods when used for the detection of the development of local or systemic infection, in particular of the detection of the development of sepsis, are a further object of the invention.

A preferred method for the determination of PSP/reg in human body fluids, e.g. serum or plasma, is an ELISA. In one embodiment of the invention, the PSP/reg ELISA consists of a sandwich array: conventional microtiter plates are coated with one type of antibody ("first" antibody") directed against PSP/reg. The plates are then blocked and the sample or standard is loaded. After the incubation, a different type of antibody ("second" antibody) against PSP/reg conjugated with a suitable label, e.g. an enzyme for chromogenic detection is applied. Finally the plate is developed with a substrate for the label in order to detect and quantify the label, being a measure for the presence and amount of PSP/reg. If the label is an enzyme for chromogenic detection, the substrate is a colour-generating substrate of the conjugated enzyme. The colour reaction is then detected in a microplate reader and compared to standards.

Suitable pairs of antibodies ("first" and "second" antibody) are any combination of guinea pig, rat, mouse, rabbit, goat, chicken, donkey or horse. Preferred are monoclonal antibodies, but it is also possible to use polyclonal antibodies or antibody fragments. Suitable labels are chromogenic labels, i.e. enzymes which can be used to convert a substrate to a detectable coloured or fluorescent compound, spectroscopic labels, e.g. fluorescent labels or labels presenting a visible colour, affinity labels which may be developed by a further compound specific for the label and allowing easy detection and quantification, or any other label used in standard ELISA.

Other preferred methods of PSP/reg detection are radioimmunoassay or competitive immunoassay using a single antibody and chemiluminescence detection on automated commercial analytical robots. Microparticle enhanced fluorescence, fluorescence polarized methodologies, or mass spectrometry may also be used. Detection devices, e.g. microarrays, are useful components as readout systems for PSP/reg.

PSP/reg is a protein that can be cloned from pancreatic mRNA and subcloned into a yeast expression vector. The protein can then be expressed under the control of Alcohol Dehydrogenase (ADH) promoter. A suitable expression medium may comprise methanol to induce and maintain the secretion of PSP/reg. PSP/reg is preferably purified using SP-Sepharose-cellulose by a pH and salt gradient. Such purified PSP/reg is used to prepare standard solutions for comparison with PSP/reg levels in body fluids. Polyclonal antibodies against the protein may be obtained from mice, rats, rabbits, goats, chicken, donkey, horses and guinea pigs or other suitable animals using standard methods.

The invention further relates to a kit of parts for the determination of PSP/reg for diagnosis/prediction of infection and/or inflammation of the airways and lungs comprising, for example, apparatus, reagents and standard solutions of PSP/reg. Apparatus considered are e.g. microtiter plates for ELISA, pre-coated ELISA plates, and plate covers. Reagents are those reagents particularly developed and designed for the detection of PSP/reg. Standard solutions of PSP/reg preferably contain PSP/reg synthesized according to the directions hereinbelow. The kit of parts may contain further hardware, such as pipettes, solutions such as buffers, blocking solutions and the like, filters, color tables and directions for use.

In another aspect, the invention relates to a kit for detecting bacterial exacerbation in COPD patients according to a method of the invention comprising at least one antibody directed against PSP/reg and reagents.

In another aspect, the invention relates to a kit for predicting the severity of an infection in a VAP patient and patient outcome according to a method of the invention comprising at least one antibody directed against PSP/reg and reagents.

In a further aspect, the invention relates to a kit for detecting the level of pancreatic stone protein (PSP/reg) in a body fluid sample comprising at least one antibody directed against PSP/reg and reagents.

In a further aspect, the invention relates to the use of a kit according to the invention for detecting the development of a local or systemic infection of the airways and lungs in a patient, notably the development of sepsis, for example, in a method according to the invention.

Antibodies directed against PSP/reg can be produced by standard methods in the field including polyclonal antibody production, monoclonal antibody production. Preferably, the antibodies are directed against a PSP/reg protein having the amino acid sequence of SEQ ID NO:1 or SEQ ID NO: 2.

It is shown that the level of PSP/reg is highly increased in patients during VAP with increased risk of mortality and in the case of bacterial exacerbation of COPD. The detection and quantification of serum PSP/reg is accomplished e.g. by a sandwich ELISA. Normal serum values are about 10 ng/ml. In VAP, the serum values correlate with the severity of VAP and may reach over 200 ng/ml. These values allow predicting whether a VAP patient has a good or a poor chance of survival. In COPD, the serum PSP/reg values correlate with the presence of positive bacterial sputum and are above 25 ng/ml. In both VAP and COPD, respective PSP/reg values allow predicting the need for intensive treatment including costly antibiotic treatment and prolonged stay in the intensive care unit. Compared to commercially available diagnostic assays, the PSP/reg ELISA is a reliable assay to predict severity and outcome in VAP patient, and to diagnose bacterial exacerbation of COPD.

The method of the invention and/or the kit according to the invention are useful for sorting the patients according to groups of risks regarding severity and outcome of the infection or inflammatory disease.

In VAP patients, a PSP/reg level, preferably from a sample obtained from the serum or plasma of a VAP patient below or equal to 24 ng/ml is predictive of a good chance of survival, whereas a PSP/reg level higher than or equal to 150 ng/ml, preferably higher than 180 ng/ml, more preferably higher than or equal to 200 ng/ml, more preferably higher than or equal to 250 ng/ml is associated with a high risk of mortality that could occur within a variable period comprised between 1 day to 3 years, for instance within 28 days after hospitalization.

As a consequence, regular and intensive follow-up and care, possibly including antibiotic treatment and prolonged stay, should be applied to VAP patients belonging to the group(s) of high risk(s).

In COPD patients, a PSP/reg level, preferably from a sample obtained from the serum or plasma of a COPD patient, below 25 ng/ml, more preferably below 20 mg/ml, is associated with a negative bacterial sputum, whereas a PSP/reg level equal or higher than 25 ng/ml, preferably equal or higher than 30 ng/ml, more preferably equal or higher than 50 ng/ml, is indicative of bacterial exacerbation. Regarding mortality of COPD patients, a PSP/reg level, preferably from a sample obtained from the serum or plasma of a COPD patient, below 18 ng/ml, preferably below 15 ng/ml, is associated with a low risk of mortality, whereas a PSP/reg level higher than 30 ng/ml, preferably higher than 34 ng/ml or more preferably higher than 35 ng/ml is associated with a high risk of mortality that could occur within a variable period comprised between 1 day to 3 years, for instance within 2 years after hospitalization.

As a consequence, regular and intensive follow-up and care, possibly including antibiotic treatment and prolonged stay, should be applied to COPD patients belonging to the group(s) of high risk(s).

EXAMPLES

Example 1: PSP/Reg is a Suitable Marker to Assess Disease Severity and Stratify Risk in VAP It has been investigated whether PSP/reg is predictive for survival in ventilator associated pneumonia.

Test Patients

The study included 101 patients (mean age, 56 years) with clinically diagnosed VAP. Patients deceased within 28 days were classified as non-survivors (NS). PSP/reg levels and sequential organ failure assessment (SOFA) scores were obtained on the day of VAP-onset and for 10 consecutive days. Detailed baseline characteristics for survivors and non-survivors are summarized in Table 1. Despite high antibiotic pre-treatment within 14 days prior to study inclusion (75%), respiratory specimens identified a causative organism in 74 patients (76%). The most frequent pathogens were *Staphylococcus aureus* (30%), *Pseudomonas aeruginosa* (25%) and *Klebsiella* species (13%). Appropriate initial antibiotic therapy, defined as a regimen combining an aminoglycoside or a fluoroquinolone plus a betalactam or an antipseudomonal carbapenem was applied in 86% of cases. Twenty patients (20%) died during the study period. Deaths were due to traumatic brain injury/subarachnoid hemorrhage (n=8), respiratory failure/Acute Respiratory Distress Syndrom (ARDS) (n=5), septic shock (n=3), cardiogenic shock (n=2), multiorgan failure (n=1) and acute liver failure (n=1). In 7 patients PSP/reg values at VAP-onset were missing.

TABLE 1

Demographics of 101 VAP patients at study inclusion

| Characteristics | Total n = 101 | Survivors n = 81 | Non-survivors n = 20 | p-value |
|---|---|---|---|---|
| Gender (male) (%) | 74 (74%) | 61 (76%) | 13 (65%) | 0.459 |
| Age (in years) (range) | 57 [43-70] | 55 [42-68] | 67 [52-75] | 0.033 |

TABLE 1-continued

Demographics of 101 VAP patients at study inclusion

| Characteristics | Total n = 101 | Survivors n = 81 | Non-survivors n = 20 | p-value |
|---|---|---|---|---|
| Admission | | | | |
| Medical | 53 (53%) | 41 (51%) | 12 (60%) | 0.615 |
| Elective surgery | 4 (4%) | 4 (5%) | 0 (0%) | 0.582 |
| Emergency surgery | 43 (43%) | 35 (43%) | 8 (40%) | 0.994 |
| From home | 61 (62%) | 51 (65%) | 10 (47%) | 0.291 |
| From hospital | 20 (20%) | 15 (19%) | 5 (24%) | 0.517 |
| Fom other ICU | 18 (18%) | 12 (15%) | 6 (29%) | 0.114 |
| Duration of mechanical ventilation before VAP (in days) (range) | 6 [3.5-9] | 6 [3-9] | 5.5 [4-9.8] | 0.801 |
| Antibiotics within 14 days before YAP-onset | 76 (75%) | 59 (73%) | 17 (85%) | 0.387 |
| Microbiology | | | | |
| Positive microbiological cultures (EA, BAL, PSB) | 74 (76%) | 58 (73%) | 16 (89%) | 0.226 |
| Positive blood cultures | 34 (34%) | 29 (36%) | 5 (25%) | 0.515 |
| Clinical scores at VAP-onset | | | | |
| SAPS II | 40.5 [32.3-51] | 38.0 [31-47.0] | 48 [42.0-55] | 0.002 |
| ODIN-score | 2 [1-3] | 2 [1-2] | 3 [1-4] | 0.050 |
| SOFA-score | 7.0 [6.0-9.8] | 6.0 [5-9] | 9.0 [7.0-14] | 0.002 |

Values are Means
( ): percentage values
[ ]: range
EA: endotracheal aspirates
BAL: bronchoalveolar lavage
PSB: protected specimen brush
SAPS II: simplified acute physiologic score II
ODIN: organ dysfunction and/or infection
SOFA: sepsis-related organ failure assessment Baseline Assessment and Follow-Up At time of enrollment the following information was recorded from each subject: age, gender, preexisting comorbidities, primary reason for initiating mechanical ventilation, duration of prior mechanical ventilation, antibiotic use within 14 days of VAP-onset, body temperature, heart rate, mean arterial pressure (MAP), oxygen saturation, ratio of partial pressure of arterial oxygen to the fraction of inspired oxygen ($PaO_2/FIO_2$), leukocyte count (WBC) and PSP/reg serum levels. The following indices were calculated: simplified acute physiologic score II (SAPS II), sequential related organ failure assessment (SOFA) score, organ dysfunction and/or infection (ODIN) score. During the 28-day follow-up period the following information was recorded: body temperature, heart rate, MAP, oxygen saturation, PaO2/FIO2, WBC, SOFA and ODIN; mechanical ventilation status and antibiotic use and survival throughout the 28-day study period. Serum PSP/reg levels were determined on VAP-onset and for 6 consecutive days after VAP diagnosis.

Diagnostic Criteria

Diagnosis of VAP was established on a clinical approach according to the American Thoracic Society Guidelines (Guidelines for the management of adults with hospital-acquired, ventilator-associated, and healthcare-associated pneumonia. Am J Respir Crit Care Med 2005; 171:388-416). It was defined as a new or progressive infiltrate on chest radiography associated with at least two of the following: purulent tracheal secretions, fever (body temperature >38°

C./100.4° F.), leukocytosis/-penia (leukocyte count >11000/L or <3000/μL). VAP patients were eligible for the study if they were intubated for mechanical ventilation for at least 48 hours and older than 18 years. Patients were excluded if they were pregnant, had received immunosuppressants or long-term corticosteroid therapy (above 0.5 mg/kg per day for longer than 1 month), were immunosuppressed or had a coexisting extrapulmonary infection diagnosed in the first three days requiring antibiotic therapy for more than three days.

Outcome Assessment

Follow-up was for 28 days or until death. Patients who died within 28 days after VAP-onset were classified as non-survivors (NS), all others were classified as survivors (S). No patient was lost to follow-up.

PSP/Reg Correlated with SOFA

Median [IQR] PSP/reg on VAP-onset was 38.6 ng/ml [22.2-179.0]. There was no association of PSP/reg with gender, co-morbidities (renal, pulmonary, cardiac, hematological/oncological) and gas exchange (oxygen saturation, $PaO_2/FIO_2$).

PSP/reg correlated with SOFA at VAP-onset (Spearman rank correlation coefficient 0.49; p<0.001, FIG. 1) and up to seven days (all p<0.02).

PSP/Reg Levels are Predictor of Outcome

PSP/reg concentrations in the serum or plasma were measured by immunoassay (ELISA method).

Figure 2:
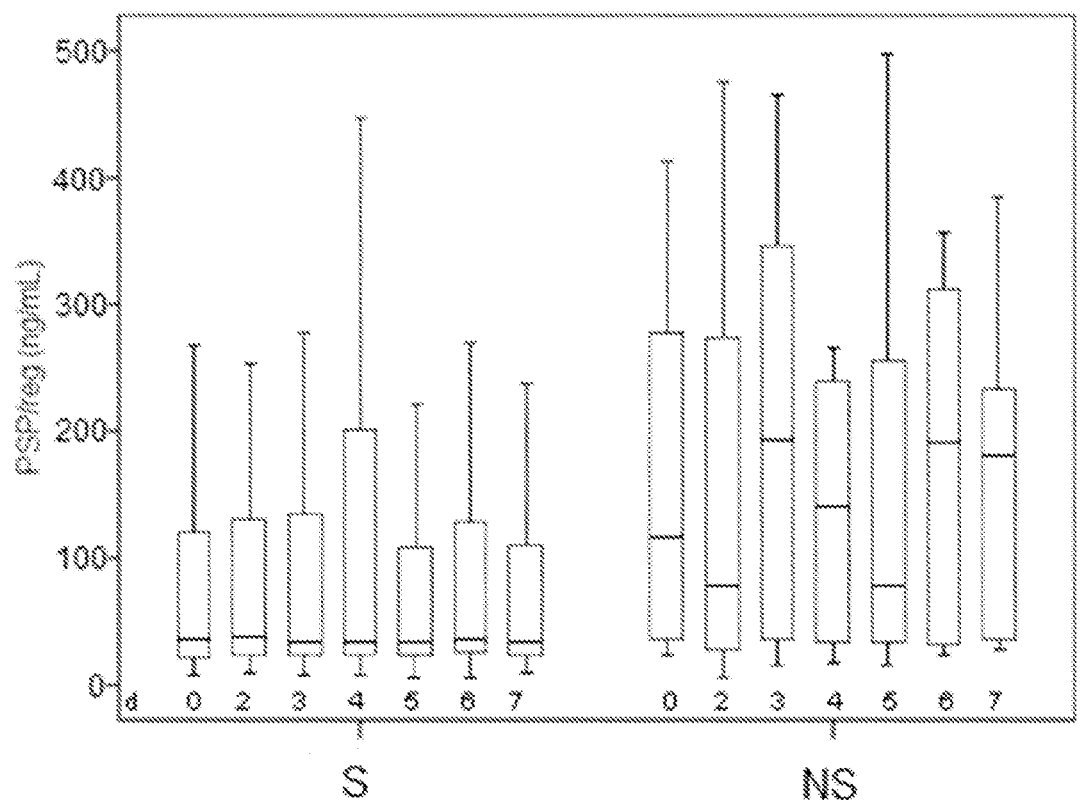
FIG. 2: Kinetics of PSP/reg serum levels in the groups of survivors (S; n=82) and non-survivors (NS; n=19) in a total of 101 patients with VAP during the first 7 days (d) after VAP-onset. Boxes represent the interquartile range (IQR), whiskers include 1.5 times the interquartile range. For clear graphical presentation outliers are not displayed. Mortality was measured at day 28.
Figure 3:
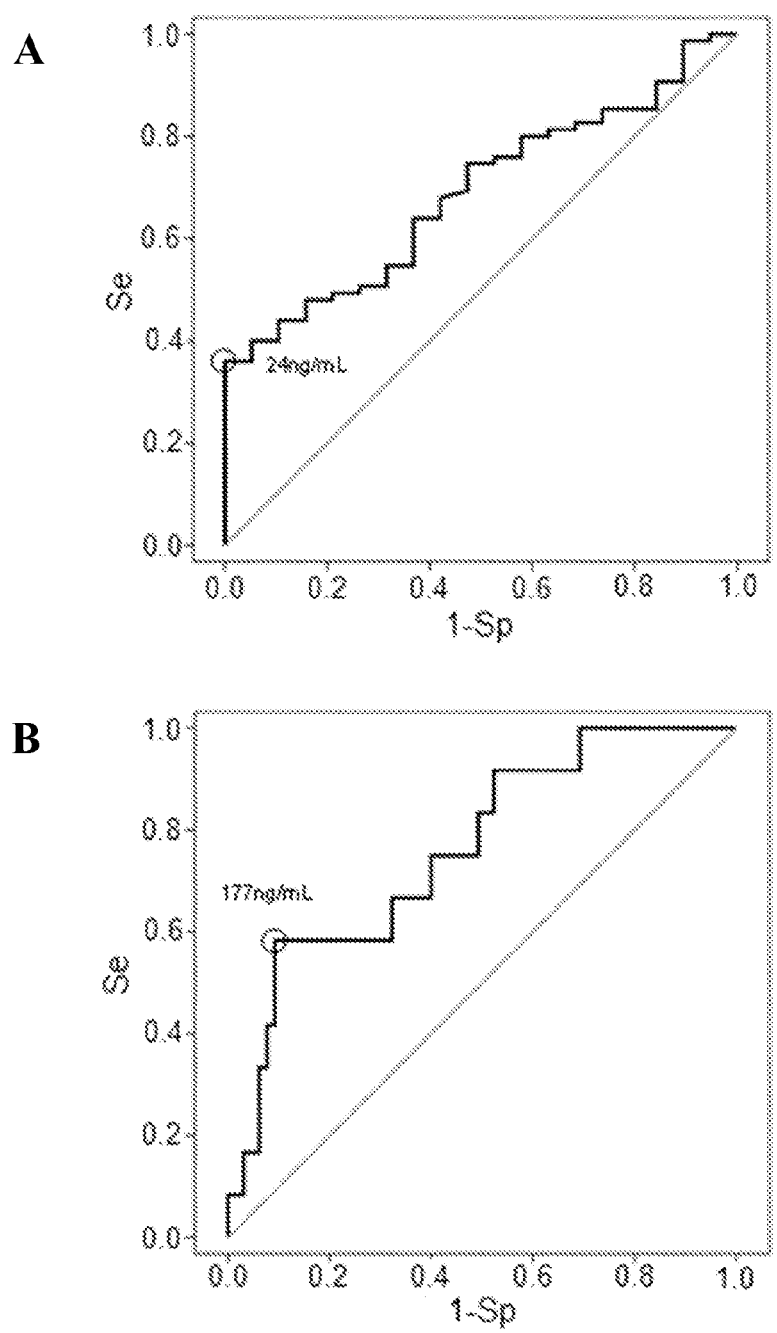
FIG. 3: PSP/reg in receiver operating characteristic (ROC) analysis: at day 0 to predict survival (A), at day 7 to predict death (B). Circles highlight the most accurate cut-offs. Using the 24 ng/ml cut-off at VAP-onset reveals a sensitivity of 36% and a specificity of 100% to predict survival (AUC: 0.69.

PSP/reg levels at VAP-onset were significantly elevated in non-survivors (median [IQR]; 117.0 ng/ml [36.1-295.3], n=19) as compared to survivors (36.3 ng/ml [21.0-124.0], n=75; p=0.011) (FIG. 2). PSP/reg tertiles at VAP-onset differed significantly in survival (log rank p=0.014). In receiver operating characteristic analysis, the area under the curve of PSP/reg for mortality/survival on VAP-onset and after 7 days were 0.69 and 0.76 (95% Confidence Interval (CI): 0.57-0.80 and 0.62-0.91), respectively (FIG. 3). PSP/reg below 24 ng/ml at VAP-onset was the most accurate threshold for predicting survival. The sensitivity was 36% and specificity 100% for predicting survival (FIG. 3A). In contrast PSP/reg above 177 ng/ml at day 7 after VAP-onset was the best cut-off to predict death (sensitivity: 58% specificity: 91%) (FIG. 3B). Positive and negative predictive values were 54% and 90%, accordingly. The odds ratio for patients PSP/reg above 177 ng/ml at day 7 to die until day 28 was 13.8 (95% Confidence Interval (CI): 3.3-57.1).

Example 2—PSP/Reg is Increased in Acute Exacerbations of COPD with Positive Sputum Culture It has been investigated whether serum and plasma PSP/reg is increased in acute exacerbations of COPD and whether PSP/reg detects positive sputum in COPD.

Test Patients 200 patients admitted to hospital for acute exacerbation of COPD were examined and were followed up for 2 years. The short and long term follow-up visits were performed 14-18 days, 6 months and 2 years after hospital admission, and comprised clinical, laboratory and lung function assessments. Clinical outcome data were obtained from medical records from hospital admission and family physicians. Patients were classified as clinical success or clinical failure. Clinical failure was defined by the occurrence of an exacerbation of COPD requiring hospitalisation or death of any cause. For survival analysis all patients were classified as survivors or non-survivors after two year follow-up. All cause mortality was assessed at 6 months and 2 years. For laboratory short- and long-term outcome inflammatory biomarkers (e.g. (PSP/reg), Procalcitonin, C-reactive protein (CRP)) were measured at initial hospital admission and during further course. PSP/reg levels were measured in serum and plasma at admission and after 14-18 days.

Study Population

Detailed baseline characteristics of the 200 patients are presented in Table 2. As suggested by the GOLD classification (Gomez and Rodriguez-Roisin, Curr. Opin. Pulm. Med. 2002: 8(2): 81-86), COPD severity as assessed at 14 days was mild in 24 (12%) patients (stage I) and moderate in 41 (21%) (stage II). Most patients had severe or very severe COPD with stage III in 82 (42%), and stage IV in 50 patients (25%). There were 100 (50%) type I, 44 (22%) type II and 56 (28%) type III exacerbations according to the Anthonisen criteria (Anthonisen et al. Ann. Intern. Med. 1987: 106(2): 196-204). Increased sputum production and discoloured sputum was present in 139 (69.5%) and 116 (58%) patients, respectively. 154 patients (77%) had at least one exacerbation. At admission, sputum samples for microbiology were obtained from 113 patients (56.5%). Sputum samples from 8 patients (7%) were from poor quality and excluded from analysis. Sputum cultures grew bacterial pathogens in 63 (56%) of cases. 42 patients (37%) had negative bacterial sputum cultures. 42 patients (68%) with positive sputum specimens were treated with antibiotics.

TABLE 2

Baseline characteristics of 200 patients presenting with an acute exacerbation of COPD

| Characteristics | N = 200 |
| --- | --- |
| Gender (male/female) (%) | 114/86 (57/43) |
| Age (in years) (range) | 70.4 (42-91) |
| Mean Duration of COPD (in months) (SD) | 125.6 (+/−83.2) |
| Duration AECOPD (in days) (SD) | 6.9 (+/−10) |
| AECOPD in previous year (at least one) (%) | 154 (77) |
| Severity of COPD & GOLD Stage (%) | |
| I (FEV1 % > 80% predicted) | 24 (12) |
| II (50% pred. > FEV1 % < 80% pred.) | 41 (21) |
| III (30% pred. > FEV1 % < 50% pred.) | 82 (42) |
| IV (FEV1 % < 30% pred.) | 50 (25) |
| FEV1 predicted (%) (SD) | 40 (+/−18.3) |
| FEV1 (Liter) (SD) | 1.07 (+/−0.52) |
| Chemistry: | |
| Leucocyte counts ×10$^9$/l | 11.1 (+/−4.8) |
| C reactive Protein (CRP) mg/dl (SD) | 35.1 (+/−46.4) |
| Procalcitonin ng/dl (SD) | 0.26 (+/−0.82) |

Values are absolute numbers (%) or means (standard deviation), when not otherwise indicated,
SD = standard deviation;
AECOPD denotes acute exacerbation of chronic obstructive lung disease;
FEV1 = forced expiratory volume in one second PSP/Reg Serum and Plasma Levels in AECOPD and Recovery Add a brief description on how the PSP/reg levels were measured, from what kind of sample.

PSP/reg concentrations in the serum or plasma were measured by immunoassay (ELISA method)

As compared to healthy controls (10.4 [7.5-12.3] ng/ml, n=38), PSP/reg was significantly increased at admission for acute exacerbation of COPD (24.3 [18.4-34.5] ng/ml). However, there was no difference between PSP/reg levels at exacerbation and at recovery (p=0.434). PSP/reg levels differed significantly across GOLD stages (p=0.011). There was a good positive correlation between PSP serum levels on initial admission and COPD severity as suggested by the GOLD classification (p=0.016). Median serum levels of PSP/reg were 20.4 ng/ml [16.9-33.6] for GOLD I, 23.8 ng/ml [18.8-32.8] for GOLD II, 26.4 ng/ml [20.6-38.8] for GOLD III and 20.8 ng/ml [16.3-29.3] for GOLD IV. PSP/reg levels correlated with C-reactive protein (p=0.031) and procalcitonin (p<0.001).

PSP/Reg Serum and Plasma Levels and Positive Sputum Bacteriology

Figure 4:
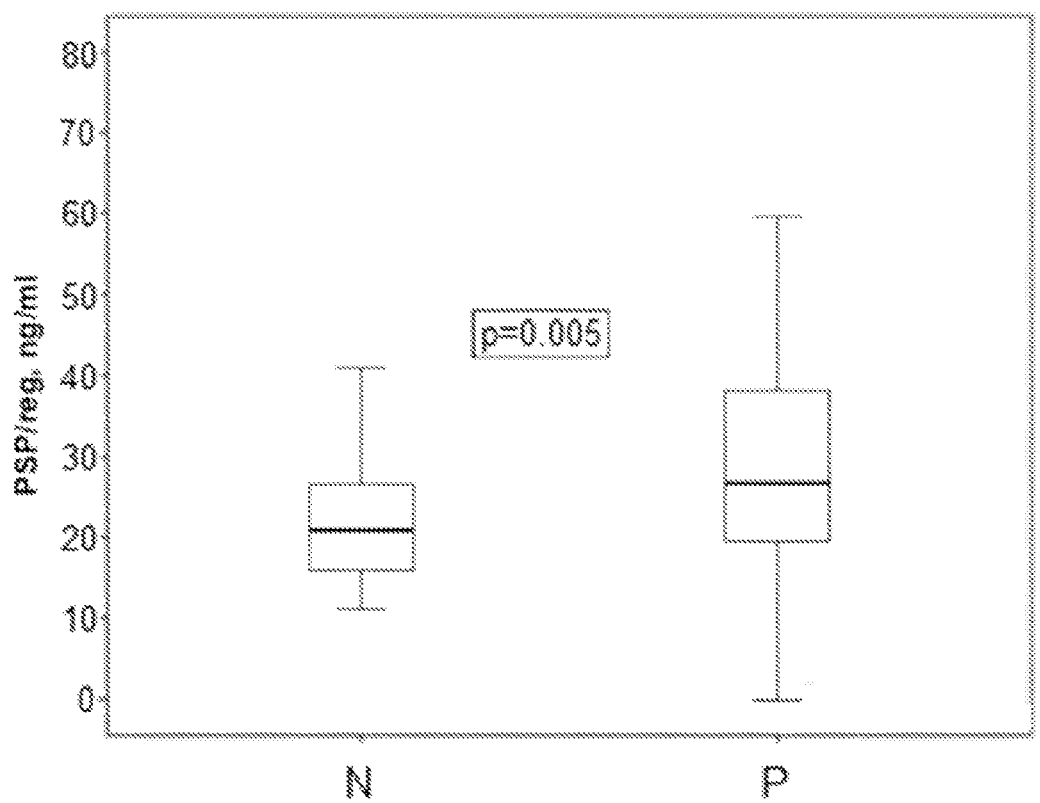
FIG. 4: PSP/reg serum levels at exacerbation of COPD according to sputum bacteriology. Patients with positive sputum bacteriology (P; n=62) had significantly higher PSP/reg serum levels as compared to patients with negative sputum bacteriology (N; n=43) (26.7 ng/ml [19.3-38.8] versus 20.8 [15.3-27.2], p=0.005).

Patients with positive and negative sputum bacterial cultures differed significantly in regard of PSP/reg serum values. Patients with positive sputum microbiology had higher levels of PSP/reg (26.7 ng/ml [19.2-38.5] vs. 20.8 ng/ml [15.6-27.2], p=0.008) (FIG. 4).

PSP/Reg and Length of Hospital-Stay and 2 Year Mortality

PSP/reg levels at exacerbation correlated significantly with the length of hospital stay (r=0.231; p=0.001). Patients with PSP/reg levels <25th percentile (<18.36 ng/ml) had a mean hospital stay from 6.9 days (±7.62) as compared to 11.34 days (±7.42) in patients presenting with levels >75th percentile (>33.86 ng/ml) on admission for exacerbation of COPD. In a Kaplan-Meier analysis to evaluate the potential of PSP/reg levels to predict short- and long-term mortality at 2-years there was a significant difference in the cumulative risk of death within the 2 years after hospitalisation for patients with lower (<18.36 ng/ml), intermediate (18.36-33.86 ng/ml) and higher PSP/reg levels (>33.86 ng/ml), (p<0.001).

The invention claimed is:

1. A method for detecting pancreatic stone protein/regenerating protein (PSP/reg) and treating VAP (ventilator-acquired pneumonia) comprising:
   a) obtaining a body fluid sample from a patient, optionally on a day of VAP onset and/or on day 2, 3, 4, 5, 6 after the VAP onset and on day 7 after the VAP onset;
   b) determining whether PSP/reg is present in said sample optionally on the day of VAP onset and/or on day 2, 3, 4, 5, 6 after the VAP onset and on day 7 after the VAP onset in a quantity equal or higher than 150 ng/ml;
   c) diagnosing the patient with VAP indicative of VAP-associated complications and an odd ratio for the patient's mortality at day 7 to day 28 of 13.8 with a 95% confidence interval when the quantity of PSP/reg present in said sample on day 7 after the VAP onset is a quantity equal or higher than 177 ng/ml, and
   d) administering an effective amount of an antibiotic to treat the diagnosed patient.

2. The method of claim 1, wherein said body fluid sample is a serum sample or a plasma sample.

3. The method of claim 1, wherein said patient is a human.

4. The method of claim 1, wherein said PSP/reg protein is SEQ ID NO:1 or SEQ ID NO: 2.

5. The method of claim 1, wherein 180 ng/ml or more PSP/reg is detected in the sample on a day of VAP onset or on day 2, 3, 4, 5, 6, or 7 after the VAP onset.

6. The method of claim 1, wherein 150 ng/ml or more of PSP/reg is detected in the sample on a day of the VAP onset or on day 2 after VAP onset.

7. The method of claim 1, wherein the patient is transferred to an intensive care unit.

8. The method of claim 1, wherein the level of PSP/reg in said body fluid sample is determined by Enzyme-linked immunosorbent assay (ELISA), Radioimmunoassay (RIA), or Enzymoimmunoassay (EIA).

9. The method of claim 1, wherein b) is performed using a first antibody directed against PSP/reg and a second antibody directed against PSP/reg conjugated with a label and wherein PSP/reg is quantified by a sandwich ELISA, wherein
   microtiter plates are coated with the first antibody directed against PSP/reg, the microtiter plates are then blocked and the sample is loaded, the second antibody against PSP/reg is applied, and the label is used to quantify the amount of PSP/reg bound to the second antibody.

10. The method of claim 9, wherein the label in the sandwich ELISA is an enzyme for chromogenic detection.

11. The method of claim 9, wherein the first and second antibody are any combination of guinea pig, rat, mouse, rabbit, goat, chicken, donkey or horse antibody.

12. A method for detecting pancreatic stone protein/regenerating protein (PSP/reg) and treating VAP (ventilator-acquired pneumonia) comprising:
   a) obtaining a body fluid sample from a patient, optionally on a day of VAP onset and/or on day 2, 3, 4, 5, 6 after the VAP onset and on day 7 after the VAP onset;
   b) determining whether PSP/reg is present in said sample optionally on the day of VAP onset and/or on day 2, 3, 4, 5, 6 after the VAP onset and on day 7 after the VAP onset;
   c) diagnosing the patient with an odd ratio for the patient's mortality resulting from VAP at day 7 to day 28 of 13.8 with a 95% confidence interval when the quantity of PSP/reg present in said sample on day 7 after the VAP onset is equal or higher than 177 ng/ml, and
   d) administering an effective amount of an antibiotic to treat the diagnosed patient.

* * * * *

SEQUENCE LISTING

```
<160> NUMBER OF SEQ ID NOS: 2

<210> SEQ ID NO 1
<211> LENGTH: 166
<212> TYPE: PRT
<213> ORGANISM: Homo sapiens

<400> SEQUENCE: 1

Met Ala Gln Thr Ser Ser Tyr Phe Met Leu Ile Ser Cys Leu Met Phe
1               5                   10                  15

Leu Ser Gln Ser Gln Gly Gln Glu Ala Gln Thr Glu Leu Pro Gln Ala
            20                  25                  30

Arg Ile Ser Cys Pro Glu Gly Thr Asn Ala Tyr Arg Ser Tyr Cys Tyr
        35                  40                  45

Tyr Phe Asn Glu Asp Arg Glu Thr Trp Val Asp Ala Asp Leu Tyr Cys
    50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Gly Thr Asp Asp Phe
                85                  90                  95

Asn Val Trp Ile Gly Leu His Asp Pro Lys Lys Asn Arg Arg Trp His
            100                 105                 110

Trp Ser Ser Gly Ser Leu Val Ser Tyr Lys Ser Trp Gly Ile Gly Ala
        115                 120                 125

Pro Ser Ser Val Asn Pro Gly Tyr Cys Val Ser Leu Thr Ser Ser Thr
    130                 135                 140

Gly Phe Gln Lys Trp Lys Asp Val Pro Cys Glu Asp Lys Phe Ser Phe
145                 150                 155                 160

Val Cys Lys Phe Lys Asn
                165

<210> SEQ ID NO 2
<211> LENGTH: 166
<212> TYPE: PRT
<213> ORGANISM: Homo sapiens

<400> SEQUENCE: 2

Met Ala Gln Thr Asn Ser Phe Phe Met Leu Ile Ser Ser Leu Met Phe
1               5                   10                  15

Leu Ser Leu Ser Gln Gly Gln Glu Ser Gln Thr Glu Leu Pro Asn Pro
            20                  25                  30

Arg Ile Ser Cys Pro Glu Gly Thr Asn Ala Tyr Arg Ser Tyr Cys Tyr
```

-continued

```
                35                  40                  45
Tyr Phe Asn Glu Asp Pro Glu Thr Trp Val Asp Ala Asp Leu Tyr Cys
    50                  55                  60

Gln Asn Met Asn Ser Gly Asn Leu Val Ser Val Leu Thr Gln Ala Glu
65                  70                  75                  80

Gly Ala Phe Val Ala Ser Leu Ile Lys Glu Ser Ser Thr Asp Asp Ser
            85                  90                  95

Asn Val Trp Ile Gly Leu His Asp Pro Lys Lys Asn Arg Arg Trp His
            100                 105                 110

Trp Ser Ser Gly Ser Leu Val Ser Tyr Lys Ser Trp Asp Thr Gly Ser
        115                 120                 125

Pro Ser Ser Ala Asn Ala Gly Tyr Cys Ala Ser Leu Thr Ser Cys Ser
        130                 135                 140

Gly Phe Lys Lys Trp Lys Asp Glu Ser Cys Glu Lys Lys Phe Ser Phe
145                 150                 155                 160

Val Cys Lys Phe Lys Asn
                165
```